US012752106B2

(12) United States Patent
Reddy et al.

(10) Patent No.: US 12,752,106 B2
(45) Date of Patent: Oct. 6, 2026

(54) CONDUCTION SYSTEM PACING LEADS AND METHODS OF MANUFACTURING (SNAP-FIT)

(71) Applicant: Cardiac Pacemakers, Inc., St. Paul, MN (US)

(72) Inventors: G. Shantanu Reddy, Minneapolis, MN (US); Andrew L. De Kock, Ham Lake, MN (US); James Finley, Minneapolis, MN (US); Alex Javier Sepulveda, Guaynabo, PR (US); Alex Felber, Prior Lake, MN (US); Lili Liu, Maple Grove, MN (US); Newell G. Voss, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 75 days.

(21) Appl. No.: 18/898,316

(22) Filed: Sep. 26, 2024

(65) Prior Publication Data

US 2025/0108207 A1 Apr. 3, 2025

Related U.S. Application Data

(60) Provisional application No. 63/586,307, filed on Sep. 28, 2023.

(51) Int. Cl.
*A61N 1/05* (2006.01)

(52) U.S. Cl.
CPC ......... *A61N 1/0575* (2013.01); *A61N 1/0573* (2013.01)

(58) Field of Classification Search
None
See application file for complete search history.

(56) References Cited

U.S. PATENT DOCUMENTS

| | | | | |
|---|---|---|---|---|
| 4,577,642 | A * | 3/1986 | Stokes ................. | A61N 1/0568 424/425 |
| 4,819,661 | A * | 4/1989 | Heil, Jr. ............... | A61N 1/0565 600/375 |
| 8,676,350 | B2 | 3/2014 | Foster et al. | |
| 2007/0179577 | A1* | 8/2007 | Marshall ................ | A61N 1/056 607/116 |
| 2014/0200640 | A1* | 7/2014 | Wulfman ............. | A61N 1/0587 607/116 |
| 2016/0059006 | A1* | 3/2016 | Doan ................... | A61N 1/0573 29/874 |

* cited by examiner

*Primary Examiner* — Kennedy Schaetzle
(74) *Attorney, Agent, or Firm* — Nelson Mullins Riley & Scarborough LLP

(57) ABSTRACT

An implantable lead includes a tubular lead body having proximal end, a distal end opposite the proximal end. A distal assembly includes an outer shell having a proximal shell component and a distal shell component. A coupler is disposed within the outer shell and includes a proximal portion having a proximal end and a first channel extending distally from the proximal end, and a distal portion opposite the proximal portion. The proximal shell component is mechanically coupled to the proximal portion of the coupler by a first snap-fit connection, and the distal shell component is mechanically coupled to the proximal portion of the coupler by a second snap-fit connection. A helical electrode is disposed about the distal portion of the coupler, and extends distally from the distal portion of the shell. First and second electrical conductors extend through the lead body and are coupled to the coupler.

20 Claims, 11 Drawing Sheets

CONDUCTION SYSTEM PACING LEADS AND METHODS OF MANUFACTURING (SNAP-FIT)

CROSS REFERENCE TO RELATED APPLICATIONS

The present application claims priority to U.S. Provisional Patent Application No. 63/586,307, filed Sep. 28, 2023, the entire disclosure of which is incorporated herein in its entirety.

TECHNICAL FIELD

The present disclosure relates to medical electrical leads and associated manufacturing methods and methods of use. In particular, the present disclosure relates to implantable medical electrical leads for stimulating the conduction system of the heart.

BACKGROUND

Cardiac rhythm management systems are useful for electrically stimulating a patient's heart to treat various cardia arrhythmias. Stimulating the native conduction system of the heart, e.g., the bundle of His, the left bundle branch and/or the right bundle branch can simultaneously pace both the right and left ventricles of the heart, potentially avoiding pacing induced dyssynchrony which may occur with right ventricular apex pacing. There is a continuing need for improved conduction system pacing designs.

SUMMARY

Example 1 is an implantable lead for use with an implantable medical device (IMD), the implantable lead comprising a tubular lead body, a proximal connector, a distal assembly, a first electrical conductor, and a second electrical conductor. The tubular lead body has proximal end, and a distal end opposite the proximal end. The proximal connector is located at the proximal end of the lead body and is configured for mechanically and electrically coupling the lead to the IMD. The distal assembly extends from the distal end of the lead body and comprises an outer shell, a coupler, a helical electrode and a ring electrode. The outer shell has a proximal shell component and a distal shell component. The coupler is made of an electrically conductive material and is disposed within the outer shell and comprises a proximal portion having a proximal end and a first channel extending distally from the proximal end, and a distal portion opposite the proximal portion, wherein the proximal shell component is mechanically coupled to the proximal portion of the coupler by a first snap-fit connection, and the distal shell component is mechanically coupled to the proximal portion of the coupler by a second snap-fit connection. The helical electrode has a proximal portion disposed about the distal portion of the coupler, and a distal portion extending distally from the distal portion of the shell. The ring electrode is disposed partially over and is mechanically coupled to the proximal shell component by a third snap-fit connection. The first electrical conductor extends through the lead body and mechanically and is electrically coupled to the coupler, the second electrical conductor extends through the lead body and is mechanically and electrically coupled to the ring electrode.

In Example 2, the implantable lead of Example 1, wherein the coupler includes a second channel extending distally form the proximal end, and a third electrical conductor is mechanically and electrically coupled to the coupler in the second channel.

In Example 3, the implantable lead of Examples 1 or 2, wherein the distal shell component overlaps the proximal shell component.

In Example 4, the implantable lead of any of Examples 1-3, wherein the first snap-fit connection is located proximal of the overlap and the second snap-fit connection is located distal of the overlap.

In Example 5, the implantable lead of any of Examples 1-4, wherein the distal shell component includes a collar impregnated with a drug or therapeutic.

In Example 6, the implantable lead of any of Examples 1-5, wherein the coupler includes a first recess, a second recess, and a flange.

In Example 7, the implantable lead of Example 6, wherein the first snap-fit connection includes a proximal shell protrusion that mates with the first recess, the second snap-fit connection includes a distal shell protrusion that mates with the second recess.

In Example 8, the implantable lead of Example 6, wherein the distal shell includes a recess configured to receive the flange.

In Example 9, the implantable lead of any of Examples 1-8, wherein the first conductor is coupled to the coupler in the first channel.

In Example 10, the implantable lead of any of Examples 1-9, wherein the proximal portion of the coupler has a first diameter and the distal portion of the coupler has a second diameter.

In Example 11, the implantable lead of Example 10, wherein the first diameter is larger than the second diameter.

In Example 12, the implantable lead of any of Examples 1-11, wherein the distal portion of the helical electrode extends from the distal portion of the shell a distance in the range of 0.5 mm to 2.5 mm.

In Example 13, the implantable lead of any of Examples 1-12, wherein an outer surface of the ring electrode, an outer surface of the proximal shell component, and an outer surface of the distal shell component are flush.

In Example 14, the implantable lead of any of Examples 1-13, wherein the distal shell component has an outer diameter that tapers from a proximal end to a distal end thereof.

In Example 15, the implantable lead of any of Examples 1-14, wherein the third snap-fit connection includes a proximal shell protrusion that mates with a recess on an interior of the ring electrode.

Example 16 is an implantable lead for use with an implantable medical device (IMD), the implantable lead comprising a tubular lead body, a proximal connector, a distal assembly, and a first electrical conductor. The tubular lead body has proximal end, a distal end opposite the proximal end, a first lead body lumen extending from the proximal end through the distal end, and a second lead body lumen extending from the proximal end through the distal end. The proximal connector is located at the proximal end of the lead body and is configured for mechanically and electrically coupling the lead to the IMD. The distal assembly extends from the distal end of the lead body and comprises an outer shell, a coupler, and a helical electrode. The outer shell has a proximal shell component and a distal shell component. The coupler is made of an electrically conductive material and is disposed within the outer shell and comprises a proximal portion having a proximal end and a first channel extending distally from the proximal end, and a distal portion opposite the proximal portion. The proximal shell component is mechanically coupled to the proximal portion of the coupler by a first snap-fit connection, and the distal shell component is mechanically coupled to the proximal portion of the coupler by a second snap-fit connection. The helical electrode has a proximal portion disposed about the distal portion of the coupler, and a distal portion extending distally from the distal portion of the shell. The first electrical conductor extends through the first lead body lumen and is mechanically and electrically coupled to the coupler within the first channel.

In Example 17, the implantable lead of Example 16, wherein the coupler includes a second channel extending distally form the proximal end, and a third electrical conductor extends through the second lead body lumen and is mechanically and electrically coupled to the coupler in the second channel.

In Example 18, the implantable lead of Example 16, wherein the distal shell component overlaps the proximal shell component.

In Example 19, the implantable lead of Example 18, wherein the first snap-fit connection is located proximal of the overlap and the second snap-fit connection is located distal of the overlap.

In Example 20, the implantable lead of Example 16, wherein the distal shell component includes a collar impregnated with a drug or therapeutic.

In Example 21, the implantable lead of Example 16, wherein the coupler includes a first recess, a second recess, and a flange.

In Example 22, the implantable lead of Example 21, wherein the first snap-fit connection includes a proximal shell protrusion that mates with the first recess, the second snap-fit connection includes a distal shell protrusion that mates with the second recess.

In Example 23, the implantable lead of Example 21, wherein the distal shell includes a recess configured to receive the flange.

In Example 24, the implantable lead of Example 16, wherein the proximal portion of the coupler has a first diameter and the distal portion of the coupler has a second diameter.

In Example 25, the implantable lead of Example 24, wherein the first diameter is larger than the second diameter.

In Example 26, the implantable lead of Example 16, wherein the distal portion of the helical electrode extends from the distal portion of the shell a distance in the range of 0.5 mm to 2.5 mm.

In Example 27, the implantable lead of Example 16, wherein the distal shell component has an outer diameter that tapers from a proximal end to a distal end thereof.

In Example 28, the implantable lead of Example 16, further comprising a ring electrode, wherein the third snap-fit connection includes a proximal shell protrusion that mates with a recess on an interior of the ring electrode.

Example 29 is a distal assembly for a lead body, the distal assembly comprising an outer shell, a coupler, a helical electrode and a ring electrode. The outer shell has a proximal shell component and a distal shell component. The coupler is made of an electrically conductive material and is disposed within the outer shell and comprises a proximal portion having a proximal end and a first channel extending distally from the proximal end and configured to receive a first electrical conductor, and a distal portion opposite the proximal portion, wherein the proximal shell component is mechanically coupled to the proximal portion of the coupler by a first snap-fit connection, and the distal shell component is mechanically coupled to the proximal portion of the coupler by a second snap-fit connection. The helical electrode has a proximal portion disposed about the distal portion of the coupler, and a distal portion extending distally from the distal portion of the shell. The ring electrode is disposed partially over and is mechanically coupled to the proximal shell component by a third snap-fit connection.

In Example 30, the distal assembly of Example 29, wherein the coupler includes a second channel extending distally form the proximal end and configured to receive a second conductor.

In Example 31, the distal assembly of Example 29, wherein the distal shell component overlaps the proximal shell component.

In Example 32, the distal assembly of Example 31, wherein the first snap-fit connection is located proximal of the overlap and the second snap-fit connection is located distal of the overlap.

In Example 33, the distal assembly of Example 29, wherein the distal shell component includes a collar impregnated with a drug or therapeutic.

Example 34 is an implantable lead for use with an implantable medical device (IMD), the implantable lead comprising a tubular lead body, a proximal connector, a distal assembly, a coiled first electrical conductor, and a stranded cable second electrical conductor. The tubular lead body has proximal end, a distal end opposite the proximal end, a first lead body lumen extending from the proximal end through the distal end, and a second lead body lumen extending from the proximal end through the distal end. The proximal connector is located at the proximal end of the lead body and is configured for mechanically and electrically coupling the lead to the IMD. The distal assembly extends from the distal end of the lead body and comprises an outer shell, a coupler, and a helical electrode. The outer shell has a proximal shell component and a distal shell component. The coupler is made of an electrically conductive material and is disposed within the outer shell and comprises a proximal portion and a distal portion opposite the proximal portion, the proximal portion having a proximal end, a first channel extending distally from the proximal end, and a second channel extending distally from the proximal end, wherein the proximal shell component is mechanically coupled to the proximal portion of the coupler by a first snap-fit connection, and the distal shell component is mechanically coupled to the proximal portion of the coupler by a second snap-fit connection. The helical electrode has a proximal portion disposed about the distal portion of the coupler, and a distal portion extending distally from the distal portion of the outer shell. The coiled first electrical conductor extends through the first lead body lumen and is mechanically and electrically coupled to the coupler within the first channel. The stranded cable second conductor extends through the second lead body lumen and is mechanically and electrically coupled to the coupler within the second channel.

In Example 35, the implantable lead of Example 34, wherein the distal assembly further comprises a ring electrode disposed partially over and mechanically coupled to the proximal shell component by a third snap-fit connection.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
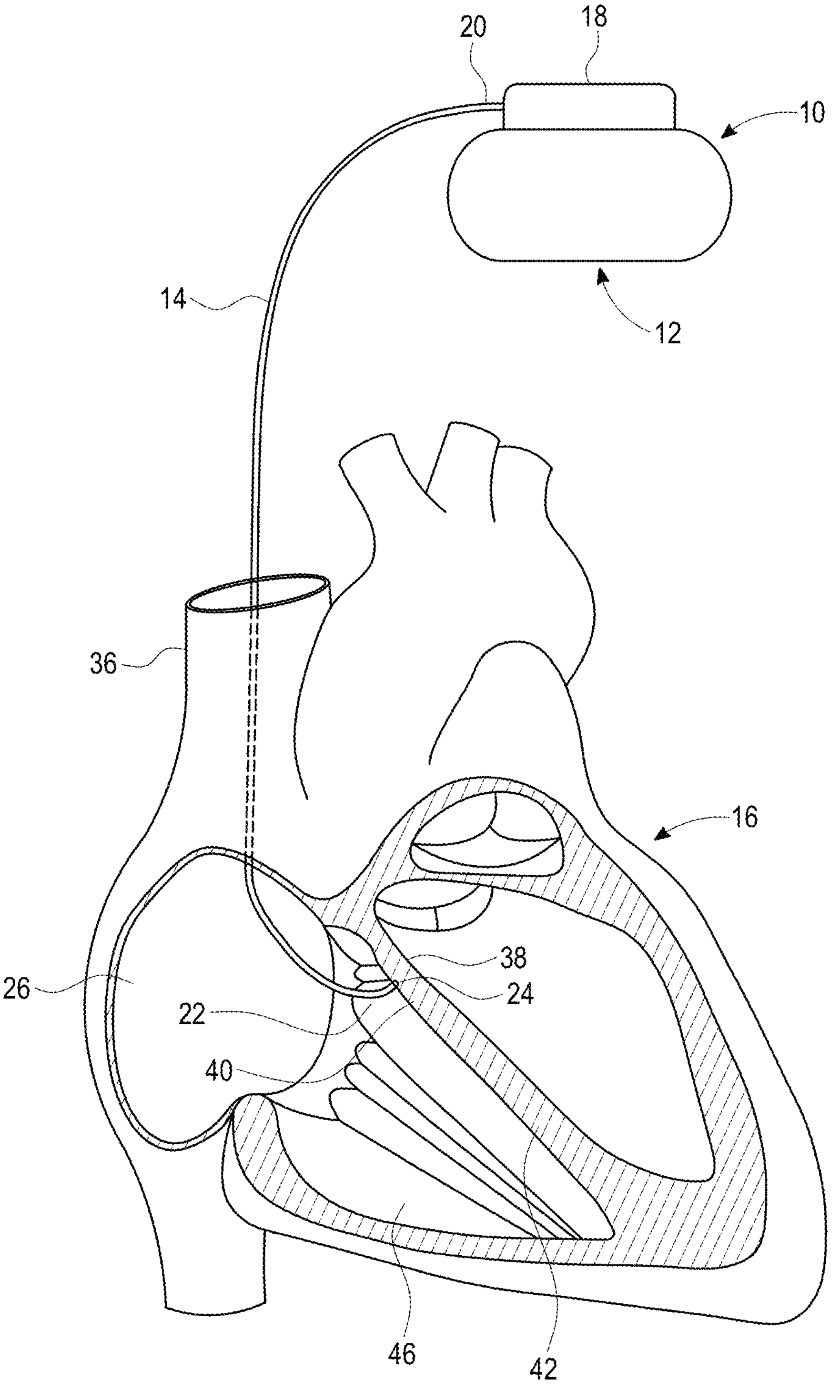
FIG. 1 is a schematic diagram of a conduction system pacing (CSP) system, according to some embodiments of this disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The present disclosure concerns, among other things, using the heart's specialized conduction system. In particular, the present disclosure concerns medical electrical leads having one or more electrodes configured to be secured in contact with, or proximate, the nerve fibers of the native conduction system, in particular the left and/or right bundle branches of the heart.

FIG. 1 is a schematic diagram of a conduction system pacing (CSP) system, according to some embodiments of this disclosure. FIG. 1 illustrates a CSP system 10 including an implantable pulse generator 12 and a lead 14. The lead 14 is implanted in a heart 16. The implantable pulse generator 12 can include circuitry for sensing bioelectrical signals and/or delivering electrical stimulation via the lead 14. The implantable pulse generator 12 can include a lead interface 18 (e.g., a header). The lead 14 can include a proximal end 20, a distal end 22, and a fixation element 24 disposed at the distal end 22.

The lead 14 can further include a proximal connector having one or more electrical contacts (not shown) at the proximal end 20, one or more electrical elements (e.g. ring electrodes) at the distal end 22, and one or more electrical conductors (e.g., one or more coils or one or more cable conductors) (not shown) extending within one or more lumens extending within the lead 14 from the electrical contacts to the electrical elements. The lead interface 18 can connect the pulse generator 12 to the electrical contacts at the proximal end 20 of the lead 14 to electrically connect the pulse generator 12 to the electrical elements.

As shown in FIG. 1, the lead 14 is implanted in a right ventricle 46, at a ventricular septum 42, proximate a left bundle branch 38 and/or right bundle branch 40 of the specialized conduction system. The lead 14 operates to convey electrical signals between the target nerve(s), e.g., the left bundle branch 38 and/or the right bundle branch 40 and the implantable pulse generator 12. In some embodiments, the lead 14 can enter the vascular system through a vascular entry site (not shown) formed in a wall of the left subclavian vein (not shown), extend through the left brachiocephalic vein (not shown) and the superior vena cava 36, to the right ventricle 46. Other suitable vascular access sites may be used in various other embodiments.

The fixation element 24 can fix the lead 14 to cardiac tissue, such as the area of tissue by which the left bundle branch 38 and/or the right bundle branch 40 can be directly stimulated. In some embodiments, the fixation element 24 can be electrically coupled to the implantable pulse generator 12 by, for example, one of the electrical conductors, such as a coil, extending to the proximal end 20 of the lead 14 for interfacing with the lead interface 18. As such, the fixation element 24 can mechanically and electrically couple the lead 14 to the tissue and facilitate the transmission of electrical energy from the conduction system in a sensing mode and to conduction system in a stimulation mode. In some embodiments, the fixation element 24 is a fixed fixation element, such as helix fixed to the lead 14. Such a fixation element 24 can be deployed by rotating the lead 14 itself to implant the fixation element 24 into the tissue. The use of the active fixation element for the fixation element 24 may allow for precise placement of the lead 14. The use of the active fixation element for the fixation element 24 may also provide for mapping capability because the user need not be concerned with accidental entanglement of the helix in the tissue.

While FIG. 1 only shows a single lead connected to the implantable pulse generator 12 and implanted for cardiac stimulation, various other embodiments can have an alternative lead and/or one or more additional leads for sensing bioelectrical activity and/or stimulating other areas of the heart 16.

In some embodiments, as will be discussed in greater detail herein, the CSP system 10 can be capable of both pacing and defibrillation therapies. In such embodiments, the lead 14 can also include one or more high voltage defibrillation electrodes (not shown in FIG. 1) for delivering defibrillation shocks capable of terminating ventricular fibrillation.

Figure 2A:
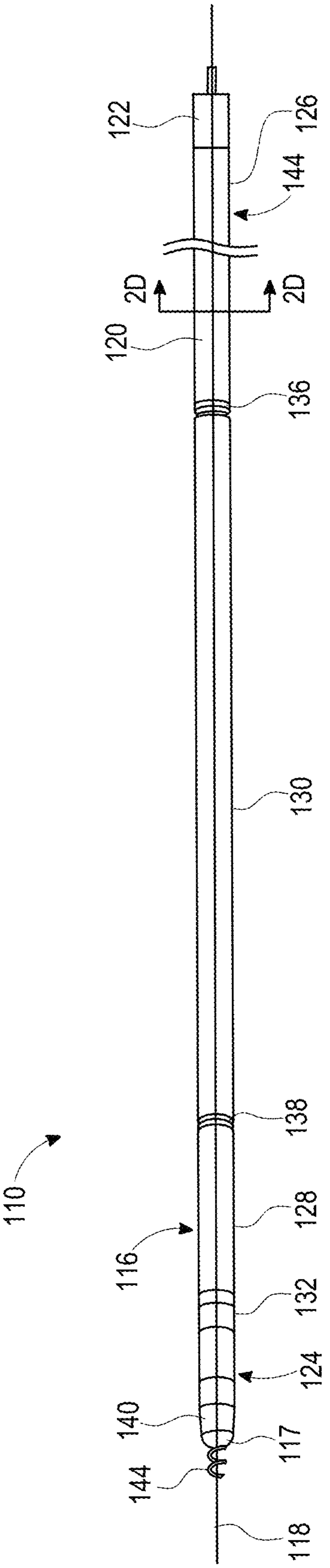
FIG. 2A is a plan view of a lead of FIG. 1, in accordance with embodiments of the subject matter of the disclosure.

FIG. 2A is a perspective view of a lead 110, in accordance with embodiments of the subject matter of the disclosure. The lead 110 has a proximal region 114, a distal region 116 terminating in a distal tip 117, and a longitudinal axis 118. Generally speaking, the proximal region 114 is dimensioned so as to make up the portion of the lead 110 extending from the pulse generator 12 to the location at which the lead 110 enters the right atrium 26 via the superior vena cava 36, whereas the distal region 116 is dimensioned to extend within the heart 16 to the location at which the lead 110 is attached to the interior of the heart 16 (see FIG. 1).

As shown, the lead 110 is composed of a flexible, elongate lead body 120, a proximal connector 122, and a distal assembly 124. The flexible elongate lead body 120 generally defines the longitudinal axis 118 of the lead 110. As further shown, the lead body 120 has a proximal end 126 and a distal end 128 opposite the proximal end 126. Additionally, the connector 122 is located at the proximal end 126 of the lead body 120, and the distal assembly 124 is located at and extends from the distal end 128 of the lead body 120. In embodiments, the connector 122 may include a terminal pin and one or more contact to electrically connect one or more active electrodes to the implantable pulse generator 12. In some embodiments, the connector 122 is a conventional bi-polar connector. In other embodiments, e.g., a quadripolar lead, the connector 122 will be configured accordingly.

In the illustrated embodiment, the lead 110 includes a shocking coil 130 positioned along the distal region 116. As shown, the shocking coil 130 is positioned between a first shocking coil coupling 136 and a second shocking coil coupling 138.

Figure 2B:
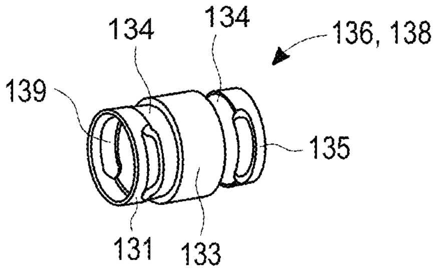
FIG. 2B is a perspective view of components of the lead in FIG. 2A, in accordance with embodiments of the subject matter of the disclosure.
Figure 2C:
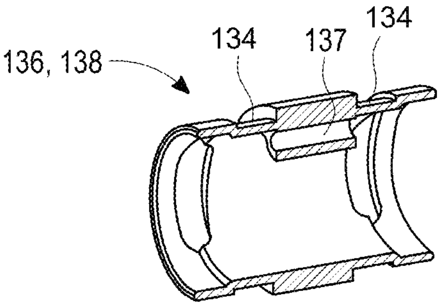
FIG. 2C is a cross-sectional view of the components of FIG. 2B, in accordance with embodiments of the subject matter of the disclosure.

FIG. 2B is a perspective view of a shocking coil coupling 136, 138, and FIG. 2C illustrates a cross-section of a shocking coil coupling 136, 138. As shown in FIG. 2B, the shocking coil coupling 136, 138 includes a first portion 131, a second portion 133, and a third portion 135. The first portion 131 and the third portion 135 have an outer surface that has a diameter smaller than the diameter of the outer surface of the second portion 133. The first portion 131 and the third portion 135 include a recess 134 formed of a further reduced diameter portion. Each recess 134 is located adjacent the second portion 133. The outer surface of the second portion is configured to be substantially the same as the outer surface of the shocking coil and the flexible elongate body 120. The first portion 131 and the third portion 135 are configured to be overlapped by the shocking coil 130 or a polymeric tube forming the flexible elongate body 120. Openings 139 allow for material to flow into the shocking coil couplings 136, 138 to securely couple the shocking coil couplings 136, 138 and, consequently, the shocking coil 130, to the lead 110. The openings 139 are formed partially within the recesses 134. The first shocking coil coupling 136 or the second shocking coil coupling 138 includes a channel 137 as shown in FIG. 2C configured to receive an electrical conductor. The electrical conductor mechanically and electrically connects the shocking coil 130 to the implantable pulse generator 12.

Figure 2D:
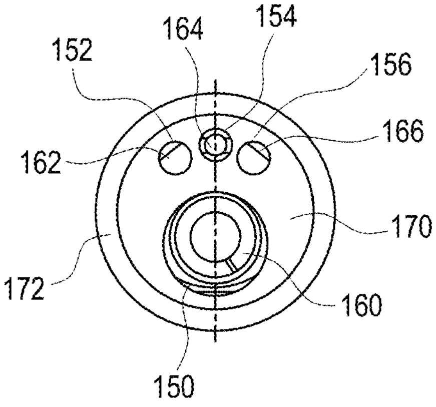
FIG. 2D is a cross sectional view of a portion of the lead of FIG. 2A, in accordance with an embodiment of the present disclosure.
Figure 2E:
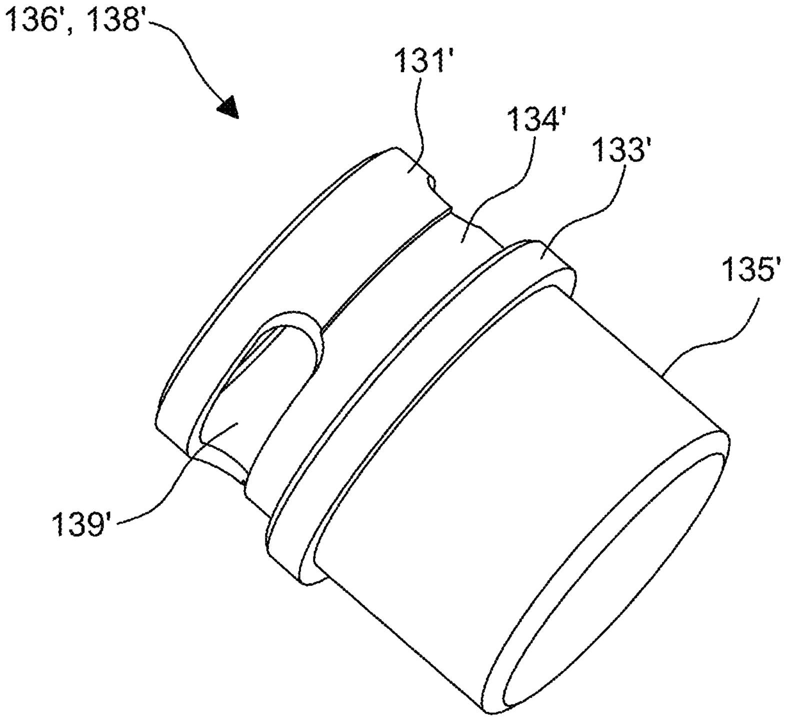
FIG. 2E is a perspective view of alternate components of the lead in FIG. 2A, in accordance with embodiments of the subject matter of the disclosure.
Figure 2F:
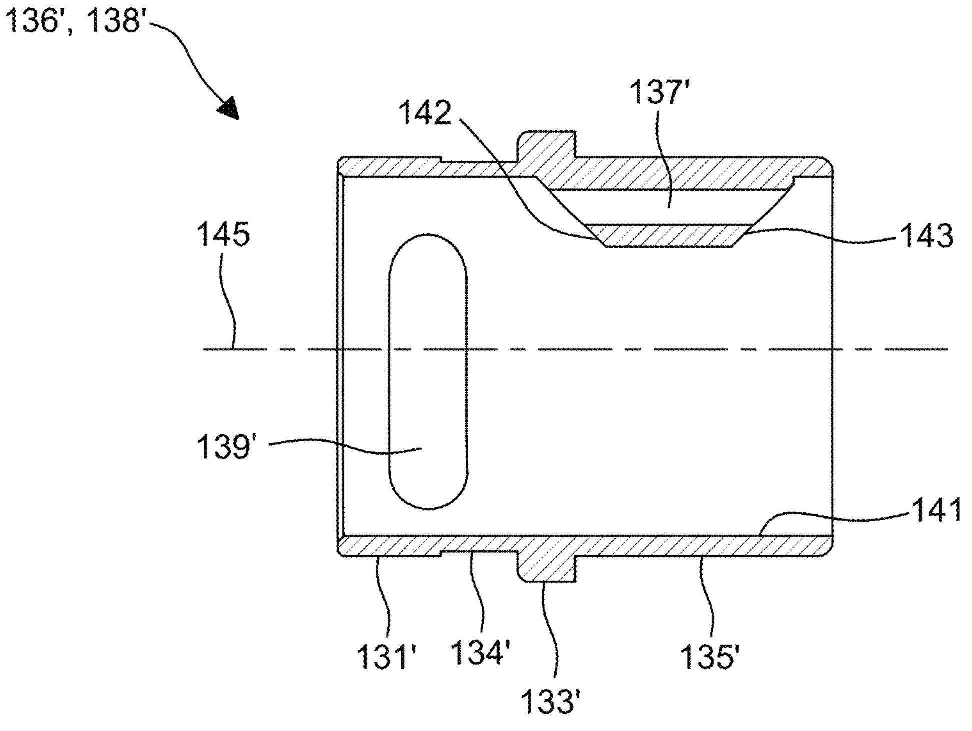
FIG. 2F is a cross-sectional view of the components of FIG. 2E, in accordance with embodiments of the subject matter of the disclosure.

FIG. 2E is a perspective view of an alternate arrangement for a shocking coil coupling 136', 138', and FIG. 2F illustrates a cross-section of the alternate arrangement for a shocking coil coupling 136', 138'. As shown in FIG. 2E, the shocking coil coupling 136', 138' includes a first portion 131', a second portion 133', and a third portion 135'. The first portion 131' and the third portion 135' have an outer surface that has a diameter smaller than the diameter of the outer surface of the second portion 133'. The first portion 131' includes a recess 134' formed of a further reduced diameter portion. The recess 134' is adjacent the second portion 133'. The outer surface of the second portion 133' is configured to be substantially the same as the outer surface of the shocking coil and the flexible elongate body 120. The first portion 131' and the third portion 135' are configured to be overlapped by or abutted against the shocking coil 130 or a polymeric tube forming the flexible elongate body 120. Openings 139' in the first portion 131' allow for material to flow into the shocking coil couplings 136', 138' to securely couple the shocking coil couplings 136', 138' and, consequently, the shocking coil 130, to the lead 110. The openings 139' are formed partially within the recess 134'. The third portion 135' includes a smooth outer surface and is void of any openings or recesses.

The first shocking coil coupling 136' and/or the second shocking coil coupling 138' includes a channel 137' as shown in FIG. 2F configured to receive an electrical conductor. The electrical conductor mechanically and electrically connects the shocking coil 130 to the implantable pulse generator 12. The channel 137' is located on an inner surface 141 of the shocking coil coupling 136', 138'. The channel 137' is located beneath the second portion 133' and the third portion 135' and extends between the second portion 133' and the third portion 135'. The channel 137' includes a first end having a first ramped surface 142 and a second end having a second ramped surface 143. The first ramped surface 142 and the second ramped surface 143 angle towards a longitudinal axis 145 extending through the shocking coil coupling 136', 138'.

Referring again to FIG. 2A, a ring electrode 132 is also included along the distal region 122. In some embodiments, the ring electrode 132 may be entirely surrounded by insulation rendering the ring electrode 132 inactive. The ring electrode is mechanically and electrically connected to the implantable pulse generator 12 by an electrical conductor that is joined to the ring electrode 132.

The distal region 116 also includes a helical electrode 144 that extends distally from the distal tip 117 of the lead 110. In embodiments, the helical electrode 144 is configured to operate as a fixation element that can be rotated into tissue in order to fix the lead 110 to a desired portion of the interior of the heart 16. Additionally, in embodiments, the helical electrode 144 is configured to be used to sense the electrical activity of the heart 16 or to apply a stimulating pulse to the cardiac tissue. This would enable a physician to use the helical electrode 144 to map cardiac tissue and thereby identify an optimal attachment site. In other embodiments, the fixation helix is not electrically active and merely operates as a fixation means.

The distal region 116 also includes a drug collar 140 located on the distal assembly 124. The drug collar 140 includes an exposed surface and is impregnated with a drug or therapeutic. The drug collar 140 is configured to deliver a drug or therapeutic to a desired tissue within the heart 16. In some embodiments, the drug collar 140 is an overmolded collar. In some embodiments, the drug collar 140 is a preformed collar.

FIG. 2D is a cross-sectional view of the lead 110 taken along the lines 2D-2D in FIG. 2A, illustrating the construction of the lead body 120 according to some embodiments of the present disclosure. As shown, in the illustrated embodiment, the lead body 120 is a quad-lumen design having a first lumen 150, a second lumen 152, a third lumen 154, and a fourth lumen 156 extending therethrough. As shown, the first lumen 150 receives a first conductor 160, which in the illustrated embodiment is a coiled conductor (which can be a single or multi-filar coil), and which as explained elsewhere, can be electrically coupled to the helical electrode 144. Additionally, the second, third and fourth lumens 152, 154, 156 can each receive one additional conductor 162, 164, 166, respectively, which may be a solid or stranded cable design. In embodiments, the conductors 162, 164, 166 may be electrically coupled to one of, for example, the ring electrode 132, the shocking coil 130, or the helical electrode 144. In embodiments, one or more of the conductors 162, 164, 166 may be electrically inactive and provided only as a structural component, e.g., to provide tensile strength to the lead 110 which may be desirable in the event the lead 110 needs to be removed from the patient or re-positioned after implantation. In the illustrated embodiment, the lead body 120 is a two-part construction, including a core member 170 and an outer layer 172, which may be made of the same material or may be comprised of different materials. It is emphasized, however, that the particular, quad-lumen lead body design illustrated in FIG. 2D is exemplary only, and other lead body configurations may be utilized within the scope of the present disclosure.

Figure 3:
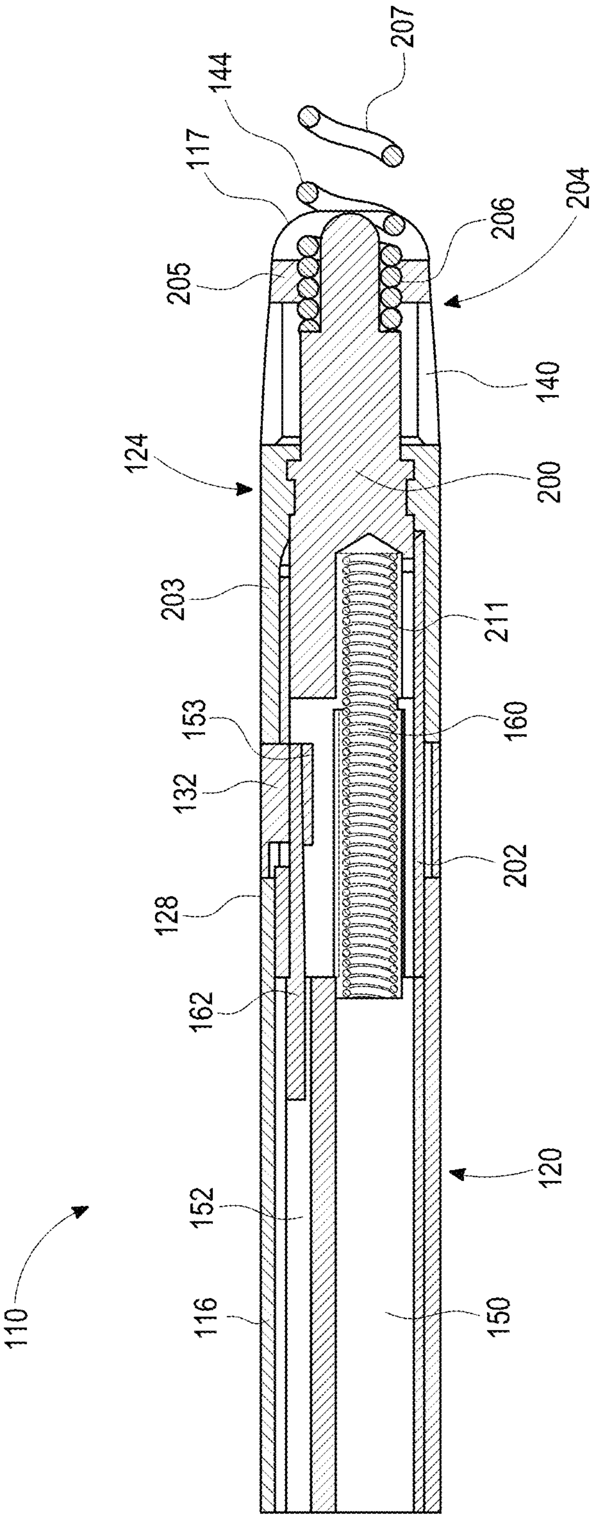
FIG. 3 is a partial cross-sectional illustration of a portion of the lead of FIG. 2A, in accordance with embodiments of the subject matter of the disclosure.

FIG. 3 is a cross sectional view of part of the distal region 116 of the lead 110, in accordance with an embodiment of the present disclosure. As shown, in the illustrated embodiment, the distal assembly 124 extends from the distal end 128 of the lead body 120, and includes a coupler 200, an inner preform 202 and an outer shell 204. The outer shell 204 includes a proximal portion 203 and a distal portion 205 that forms the distal tip 117 of the lead 110. As further shown, the helical electrode 144 has a proximal portion 206 that is secured to the coupler 200, and a distal portion 207 that extends distally from the distal tip 117 of the lead 110.

As shown, the outer shell 204 surrounds and encompasses the coupler 200 and the tubular inner preform 202, and at least the proximal portion 206 of the helical electrode 144. In embodiments, the outer shell 204 is securely fixed to the coupler 200 and the tubular inner preform 202. In the various embodiments, the outer shell 204 is formed of a polymeric material that is formed by an overmolding process, for example an injection molding process. In some embodiments, the proximal portion 203 and the distal portion 205 are formed of the same polymeric material. In some embodiments, the proximal portion 203 and the distal portion 205 are formed of different polymeric materials. In embodiments, the distal portion 205 of the outer shell 204 may comprise a drug-eluting polymer, thus obviating the need for a separately provided drug collar 140.

As further shown, in the illustrated embodiment, the drug collar 140 decreases in diameter in the proximal-to-distal direction, thus defining a taper in the distal end of the distal assembly 124. In other embodiments, the distal assembly 124 is substantially iso-diametric along substantially its entire length.

The coupler 200 is made of an electrically conductive material and is disposed within the outer shell 204. As shown, the coupler 200 includes a channel 211 extending distally from a proximal end of the coupler 200, forming a blind hole. As further shown, the first conductor 160 extends from the connector 122 (FIG. 2A) and mechanically and electrically couples with the coupler 200 within the channel 211. The first conductor 160 carries electrical pulses and signals between the implantable pulse generator 12 (FIG. 1) and the helical electrode 144 via the coupler 200. In some embodiments, the first conductor 160 is a multi-filar coiled wire and extends proximally through the lead 110 in the first lead body lumen 150.

The coupler 200 is configured to engage with the tubular inner preform 202. In some embodiments, the coupler 200 and the tubular inner preform 202 are configured to mechanically couple vie a snap-fit or other connection.

In the illustrated embodiment, the conductor 162 is disposed within the second lead body lumen 152 and is mechanically and electrically coupled to the ring electrode 132. As shown, the ring electrode 132 includes a projection 153 that extends radially inwardly and includes an opening to receive the conductor 162, which can be secured to the ring electrode 132 by any suitable means, e.g., welding, crimping, staking, and the like. In embodiments, the second conductor 212 is a stranded wire cable. The conductor 162 carries electrical pulses and signals between the implantable pulse generator 12 (FIG. 1) and the ring electrode 132.

Figure 4:
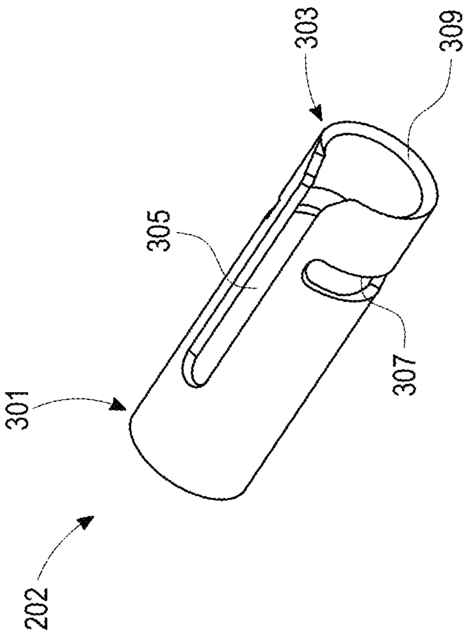
FIG. 4 is a perspective view of an inner preform of the lead of FIG. 3, in accordance with an embodiment of the present disclosure.

FIG. 4 is a perspective view of the tubular inner preform 202, in accordance with an embodiment of the present disclosure. The tubular inner preform 202 has a proximal end 301 and a distal end 303 opposite the proximal end 301. A longitudinal slot 305 extends partially along the tubular inner preform 202 from the distal end 303 toward the proximal end 301. The longitudinal slot 305 provides expansion for the inner preform 202 when being joined with coupler 200, and also receives projection 150 of ring electrode 132. A circumferential slot 307 extends partially around a circumference of the inner preform 202. The distal end 303 of the inner preform 202 includes a beveled edge 309 that aids in receiving a proximal end 401 of the coupler 200 when the tubular inner preform 202 and the coupler 200 are connected.

Figure 5:
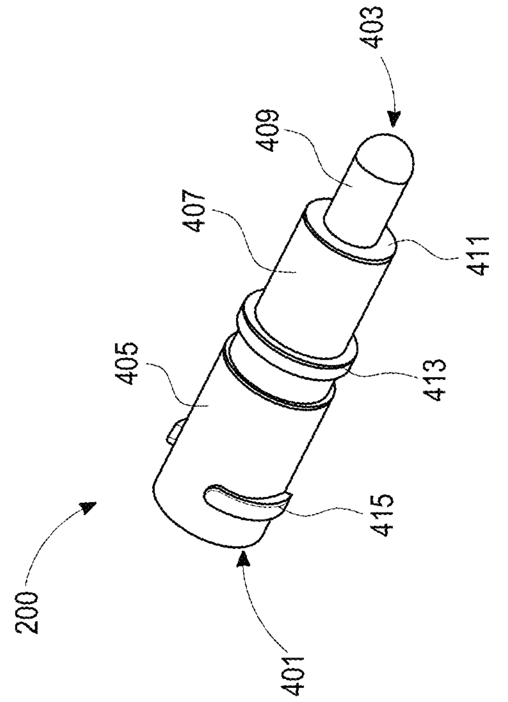
FIG. 5 is a perspective view of a coupler of the lead of FIG. 3, in accordance with an embodiment of the present disclosure.

FIG. 5 is a perspective view of the coupler 200, in accordance with an embodiment of the present disclosure. As shown, the coupler 200 includes a proximal end 401 and a distal end 403 opposite the proximal end 401. The coupler 200 includes a proximal portion 405, a distal portion 409 opposite the proximal portion 405, and an intermediate portion 407 between the proximal portion 405 and the distal portion 409. The coupler 200 includes a radial rib 415 extending partially around a circumference of the proximal portion 405 that is configured to be received within the circumferential slot 307 of the tubular inner preform 202 to couple the tubular inner preform 202 to the proximal portion 405 of the coupler 200. The intermediate portion 407 includes a radial flange 413 extending outwardly from the surface of the intermediate portion 407. The radial flange 413 provides enhanced coupling to the outer shell 204, e.g., by providing a mechanical interlock between the coupler 200 and the outer shell 204.

As shown, the proximal portion 405 of the coupler 200 has a first diameter, the intermediate portion 407 of the coupler 200 has a second diameter, and the distal portion 409 of the coupler 200 has a third diameter. In the embodiment shown in FIG. 5, the first diameter is larger than the second and third diameters. Referring back to FIG. 3, the proximal portion 206 of the helical electrode 144 is disposed about and secured to the distal portion 409 of the coupler 200, which further includes a shoulder 411 against which the helical electrode 124 abuts. Accordingly, the helical electrode 144 surrounds and extends distally from the distal portion 409 of the coupler 200.

Figure 6:
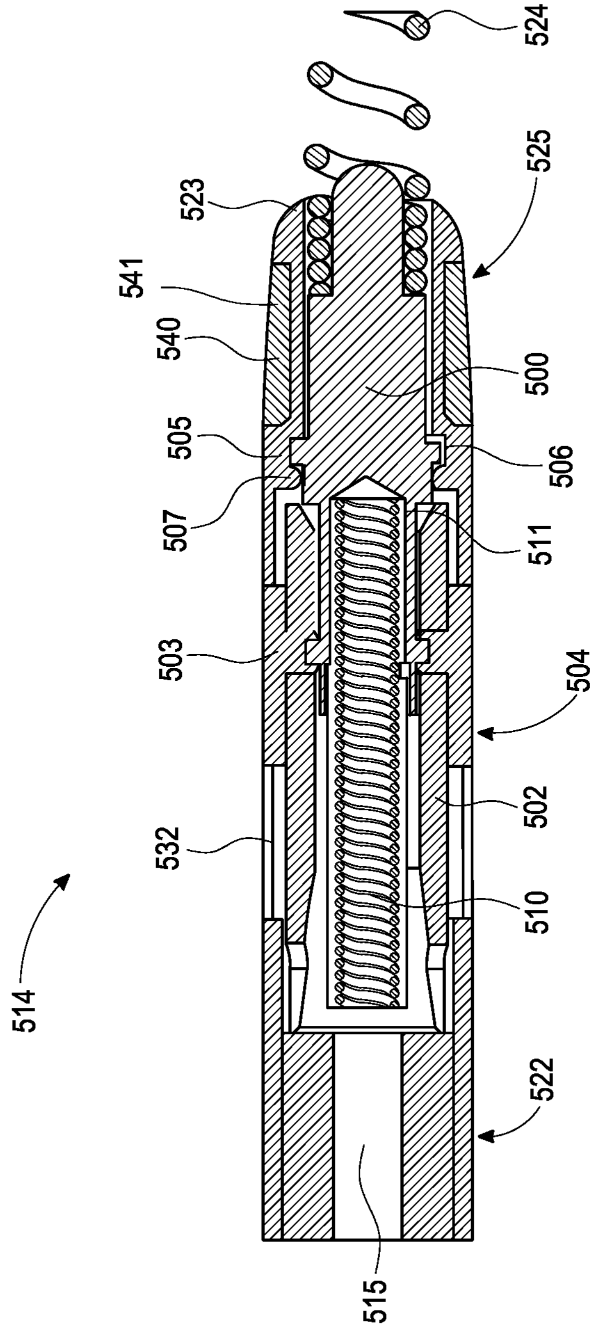
FIG. 6 is a partial cross-sectional view of a portion of an alternative lead, in accordance with an embodiment of the present disclosure.

FIG. 6 is a cross sectional view of another arrangement of a distal region 522 of an alternative lead 514, in accordance with an embodiment of the present disclosure. The lead 514 may be constructed in substantially the same manner as the lead 110 except as described in connection with FIG. 6. As shown, the outer diameter of the lead 514 is substantially the same along the distal region 522 with the exception of a tapered portion 541 adjacent a distal tip 523. The tapered portion (defined by a tapered drug collar 540 as in the lead 110 of FIG. 3) reduces in diameter towards the distal tip 523. In this arrangement, the drug collar 540 is tapered.

The distal region 522 of the lead 514 is similar to that of the lead 110 and includes a distal assembly 525 including a coupler 500, an outer shell 504, and a helical electrode 524. The outer shell 504 includes a proximal portion 503 and a distal portion 505 forming the distal tip 523. In embodiments, the proximal portion 503 is formed of a polymeric material by an overmolding process, for example an injection molding process. In the illustrated embodiment, the distal portion 505 of the outer shell 504 is a preformed component that is configured to mechanically couple to the coupler 500 at an intermediate portion thereof. As shown, the distal portion 505 includes a radial recess 506 and a protrusion 507 configured to secure the distal portion 505 to the coupler 500, as described in greater detail below. In embodiments, the distal portion 505 may be formed out of a relatively hard polymeric material such as polyether etherketone (PEEK), tecothane, or the like. In some embodiments, the proximal portion 503 and the distal portion 505 are formed of the same polymeric material. In some embodiments, the proximal portion 503 and the distal portion 505 are formed of different polymeric materials.

The outer shell 504 surrounds and encompasses at least a portion of a coupler 500, a tubular inner preform 502, and the helical electrode 524, in the same matter as in the distal assembly 124 of the lead 110. In some embodiments, the outer shell 504 may contact each of the coupler 500, the tubular inner preform 502, and the helical electrode 524. In some embodiments, the outer shell 504 may contact some, but not all of the coupler 500, the tubular inner preform 502, and the helical electrode 524.

The coupler 500 is made of an electrically conductive material and is disposed within the outer shell 504. In embodiments, the helical electrode 524 is connected to the coupler 500 in the same manner as described above in connection with the lead 110. The coupler 500 includes a channel 511 extending distally from its proximal end, forming a blind hole. A first conductor 510 extends from the connector 122 (see FIG. 2A) within a first lead body lumen 515 and mechanically and electrically couples with the coupler 500 in the channel 511. The first conductor carries electrical pulses and signals between the implantable pulse generator 12 and the helical electrode 524 via the coupler 500. In some embodiments, the first conductor 510 is a multifilar coiled wire and extends proximally through the lead 514 in a first lead body lumen 515. In embodiments, the conductor 510 may be constructed in the same manner as the conductor 110 described above.

The coupler 500 is configured to engage with the tubular inner preform 502. In some embodiments, the coupler 500 and the tubular inner preform 502 are configured to mechanically couple via a snap-fit or other connection. Additionally, the distal portion 505 of the outer shell 504 is configured to mechanically couple to the coupler 500 via a snap-fit connection.

A ring electrode 532 is located on the distal portion 522 of the lead 514. The ring electrode 532 is connected to the implantable pulse generator 12 (FIG. 1) with a second conductor (not shown) that extends proximally from the ring electrode 532.

Figure 7:
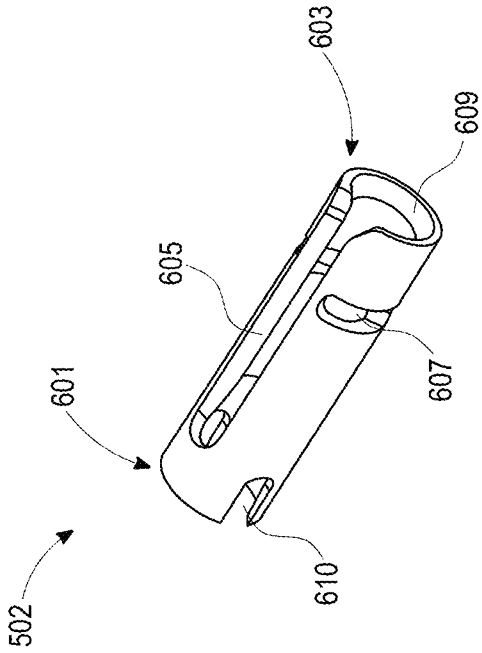
FIG. 7 is a perspective view of an inner preform of the lead of FIG. 6, in accordance with an embodiment of the present disclosure.

FIG. 7 is a perspective view of the tubular inner preform 502, in accordance with an embodiment of the present disclosure. The tubular inner preform 502 has a proximal end 601 and a distal end 603 opposite the proximal end 601. A longitudinal slot 605 extends partially along the tubular inner preform 502 from the distal end 603 toward the proximal end 601. The longitudinal slot 605 provides for expansion of the inner preform 502 when being joined with coupler 500. A circumferential slot 607 extends partially around a circumference of the inner preform 502. The distal end 603 of the inner preform 502 includes a beveled edge 609 that aids in receiving a proximal end 701 of the coupler 500 when the tubular inner preform 502 and the coupler 500 are connected. The proximal end 601 also includes a U-shaped recess 610.

Figure 8:
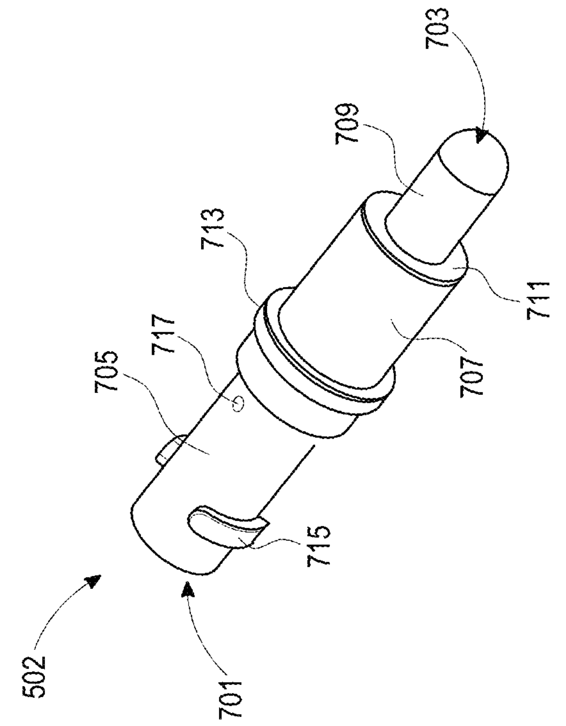
FIG. 8 is a perspective view of a coupler of the lead of FIG. 6, in accordance with an embodiment of the present disclosure.

FIG. 8 is a perspective view of the coupler 500, in accordance with an embodiment of the present disclosure. As shown, the coupler 500 has a proximal end 701 and a distal end 703 opposite the proximal end 701. In the illustrated embodiment, the distal end 703 is rounded or semi-spherical, although in other embodiments the distal end 703 may take on different shapes, e.g., flat/planar, conical or frusto-conical. As further shown, the coupler 500 includes a proximal portion 705 terminating at the proximal end 701, a distal portion 709 opposite the proximal portion 705 and terminating at the distal end 703, and an intermediate portion 707 between the proximal portion 705 and the distal portion 709. As illustrated, the coupler 500 includes a radial rib 715 extending partially around a circumference of the proximal portion 705 that is configured to be received within the circumferential slot 607 of the tubular inner preform 502 to couple the tubular inner preform 502 to the proximal portion 705 of the coupler 500.

The intermediate portion 707 of the coupler 500 includes a radial flange 713 extending outwardly from the surface of the intermediate portion 707. The radial flange 713 is configured to be received in the recess 506 in the distal portion 505 of the outer shell 504 to mechanically couple the distal portion 505 to the coupler 500 in a snap-fit arrangement (see FIG. 6). Additionally, the protrusion 507 extending inwardly from the inner surface of the distal portion 505 of the outer shell 504 operates to engage a proximal surface of the radial flange 713 and forms a portion of the snap-fit arrangement (see FIG. 6).

The proximal portion 705 of the coupler 500 has a first diameter, the intermediate portion 707 of the coupler 500 has a second diameter, and the distal portion 709 of the coupler 500 has a third diameter. In the embodiment shown in FIG. 9, the second diameter is larger than the first and third diameters. Referring as well to FIG. 6, the distal portion 709 includes a shoulder 711 which the helical electrode 524 abuts. The helical electrode 524 surrounds the distal portion 709 and extends distally from the distal portion 709. The proximal portion 705 additionally includes an aperture 717 leading to the channel 511.

Figure 9:
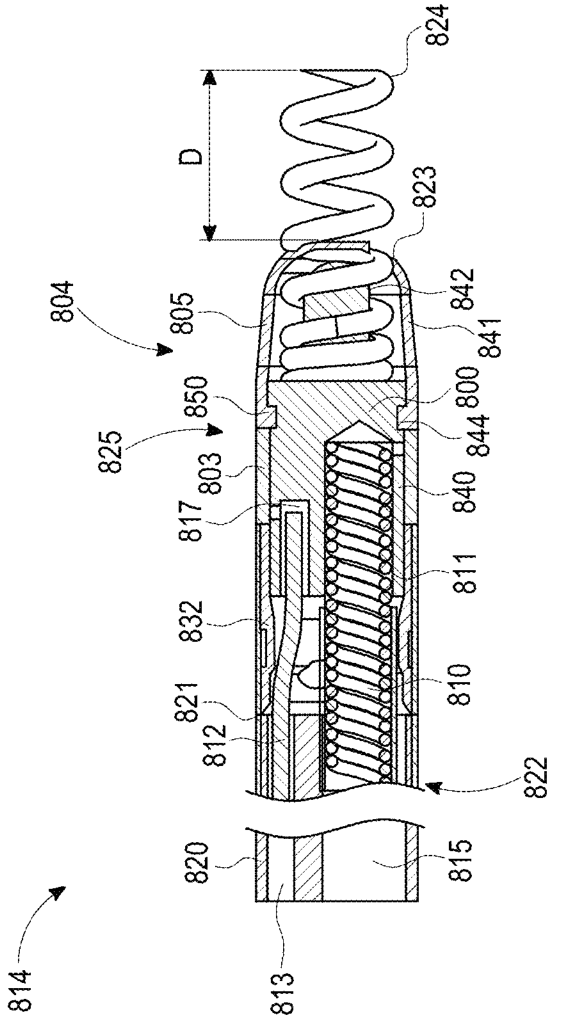
FIG. 9 is a partial cross-sectional view of portion of an alternative lead, in accordance with an embodiment of the present disclosure.

FIG. 9 is a cross sectional view of another arrangement of a distal portion 822 of lead 814, in accordance with an embodiment of the present disclosure. In embodiments, the lead 814 may be constructed in substantially the same manner as the leads 110 and 514 described above, except as described in connection with FIG. 9. As shown, the lead 814 includes a tubular lead body 820 having proximal end (not shown) and a distal end 821 opposite the proximal end. A distal assembly 825 extends from the distal end 821 of the lead body 814. A first lead body lumen 815 extends from the proximal end through the distal end 821 of the lead body 814, and a second lead body lumen 813 extends from the proximal end through the distal end 821 of the lead body 814. The first lead body lumen 815 receives a first conductor 810 and the second lead body lumen 813 receives a second conductor 812. A proximal connector at the proximal end of the lead body 820 configured for mechanically and electrically coupling the lead 814 to the IMD 12 (see FIG. 1). The first conductor 810 and the second conductor 812 mechanically and electrically connect to the IMD 12 (FIG. 1) via the proximal connector (not shown).

The distal assembly 825 includes an outer shell 804, a coupler 800, a helical electrode 824, and a ring electrode 832. The outer shell includes a proximal shell component 803 and a distal shell component 805. In some embodiments, the proximal shell component 803 takes the form of a drug collar that is impregnated with a drug or therapeutic to be delivered to target tissue in the heart. In the illustrated embodiment, the distal shell component 803 includes a tapered portion 841 that reduces in diameter towards a distal tip 823 of the lead 814.

The coupler 800 is formed of an electrically conductive material and includes a proximal portion 840 and a distal portion 842. A first channel 811 extends distally within the proximal portion 840 from its proximal end, forming a blind hole. The first channel 811 is configured to receive the first conductor 810 and facilitate mechanically and electrically coupling the first conductor 810 to the coupler 800. A second channel 817 extends distally within the proximal portion 840 from the proximal end of the coupler 800, and forms a second blind hole. The second channel 817 is configured to receive the second conductor 812, which is mechanically and electrically coupled to the coupler 800 within the second channel 817.

The helical electrode 824 includes a proximal portion that is disposed about the distal portion 842 of the coupler 800, as described elsewhere herein with other embodiments. The helical electrode 824 extends from the distal tip 823 of the lead a distance D that can be selected to optimize the particular clinical needs for conduction system pacing. In embodiments, the distance D can range from between 0.5 mm to 2.5 mm. The helical electrode 824 can receive or transfer electrical pulses to the IMD 12 via the coupler 800 and the first conductor 810 and/or the second conductor 812.

In the illustrated embodiment, the coupler 800 includes a circumferential recess 844 located near the distal end of the proximal portion 840 of the coupler 800. Additionally, a protrusion 850 extends radially inwardly at the proximal end of the distal shell component 805. As can be seen in FIG. 9, the protrusion 850 is received in the circumferential recess 844 to form a snap-fit connection between the coupler 800 and the distal shell component 805.

Figure 10:
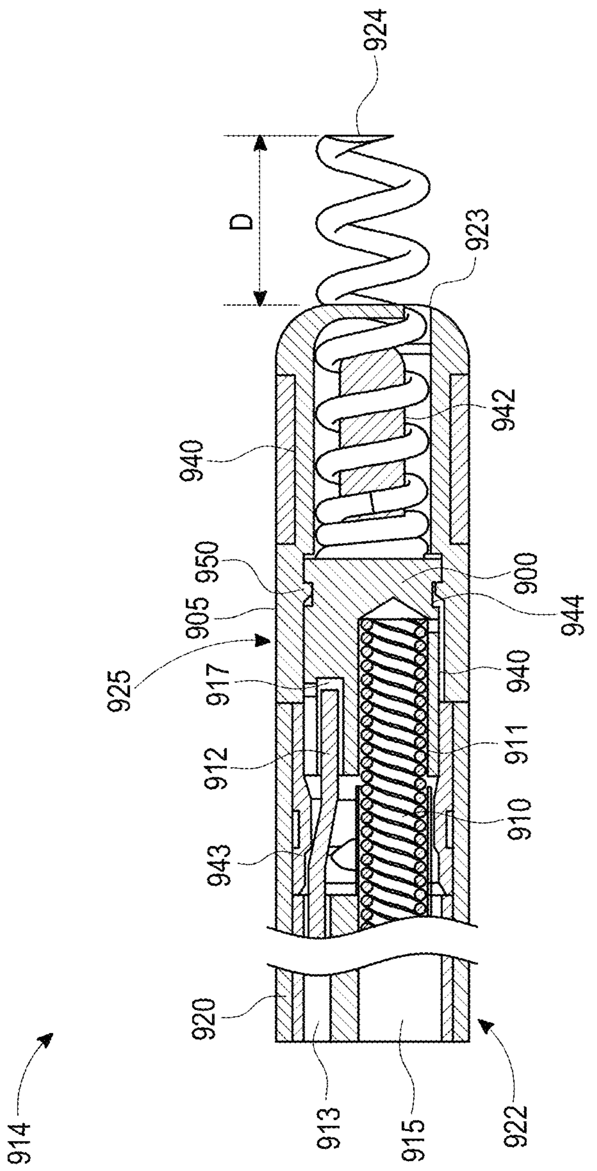
FIG. 10 is a partial cross-sectional view of portion of an alternative lead, in accordance with an embodiment of the present disclosure.

FIG. 10 is a cross sectional view of another arrangement of a distal portion 922 of lead 914, in accordance with an embodiment of the present disclosure. In embodiments, the lead 914 may be constructed in substantially the same manner as the leads 110, 514 and 814 described above, except as described in connection with FIG. 9. In the illustrated embodiment, the lead 914 includes a tubular lead body 920 having proximal end (not shown) and a distal end 921 opposite the proximal end. A distal assembly 925 extends from the distal end 921 of the lead body 920. A first lead body lumen 915 extends from the proximal end through the distal end 921 of the lead body 920, and a second lead body lumen 913 extends from the proximal end through the distal end 921 of the lead body. A first conductor 910 is received within the first lead body lumen 915, and a second conductor 912 is received within the second lead body lumen 913.

As shown, the distal assembly 925 includes an outer shell 905, a coupler 900, and a helical electrode 924. Although not shown in FIG. 10, in embodiments, the distal assembly 925 may also include one or more ring electrodes as described with respect to other embodiments. The coupler 900 is formed of an electrically conductive material and includes a proximal portion 940 and a distal portion 942. A first channel 911 extends distally within the proximal portion 940 from its proximal end, forming a blind hole. The first channel 911 is configured to receive the first conductor 910 and facilitate mechanically and electrically coupling the first conductor 910 to the coupler 900. A second channel 917 extends distally within the proximal portion 940 from the proximal end of the coupler 900, and forms a second blind hole. The second channel 917 is configured to receive the second conductor 912, which is mechanically and electrically coupled to the coupler 900 within the second channel 917. In the illustrated embodiment, a conductive support tube 943 is disposed over the proximal portion of the coupler 900 and extends proximally within the lead body 920. When present, the support tube operates as a structural interface for coupling the distal assembly 925 to the lead body 920, as well as providing structural support to the coupler 900.

As shown, the helical electrode 924 includes a proximal portion that is disposed about the distal portion 942 of the coupler 900, as described elsewhere herein with respect to other embodiments. The helical electrode 924 extends from the distal tip 923 of the lead a distance D that can be selected to optimize the particular clinical needs for conduction system pacing. In embodiments, the distance D can range from between 0.5 mm to 2.5 mm. The helical electrode 924 can receive or transfer electrical pulses to the IMD 12 via the coupler 900 and the first conductor 910 and/or the second conductor 912.

In the illustrated embodiment, the coupler 900 includes a circumferential recess 944 located near the distal end of the proximal portion 940 of the coupler 900. Additionally, a protrusion 950 extends radially inwardly at the proximal end of the outer shell 905. As can be seen in FIG. 10, the protrusion 950 is received in the circumferential recess 944 to form a snap-fit connection between the coupler 900 and the outer shell 905, similar to the embodiment described in connection with FIG. 9. As further shown in FIG. 10, in embodiments, the protrusion 950 has a sloped proximal surface to facilitate assembling the outer shell 905 and the coupler 900, i.e., by sliding the outer shell 905 over the coupler 900 in a distal-to-proximal direction. Additionally, the distal surface of the protrusion 950 is generally parallel to the wall forming the circumferential recess 944 so as to abut the wall once the snap-fit connection has been formed, thus resisting separation of the coupler 900 and the outer shell 905.

Figure 11:
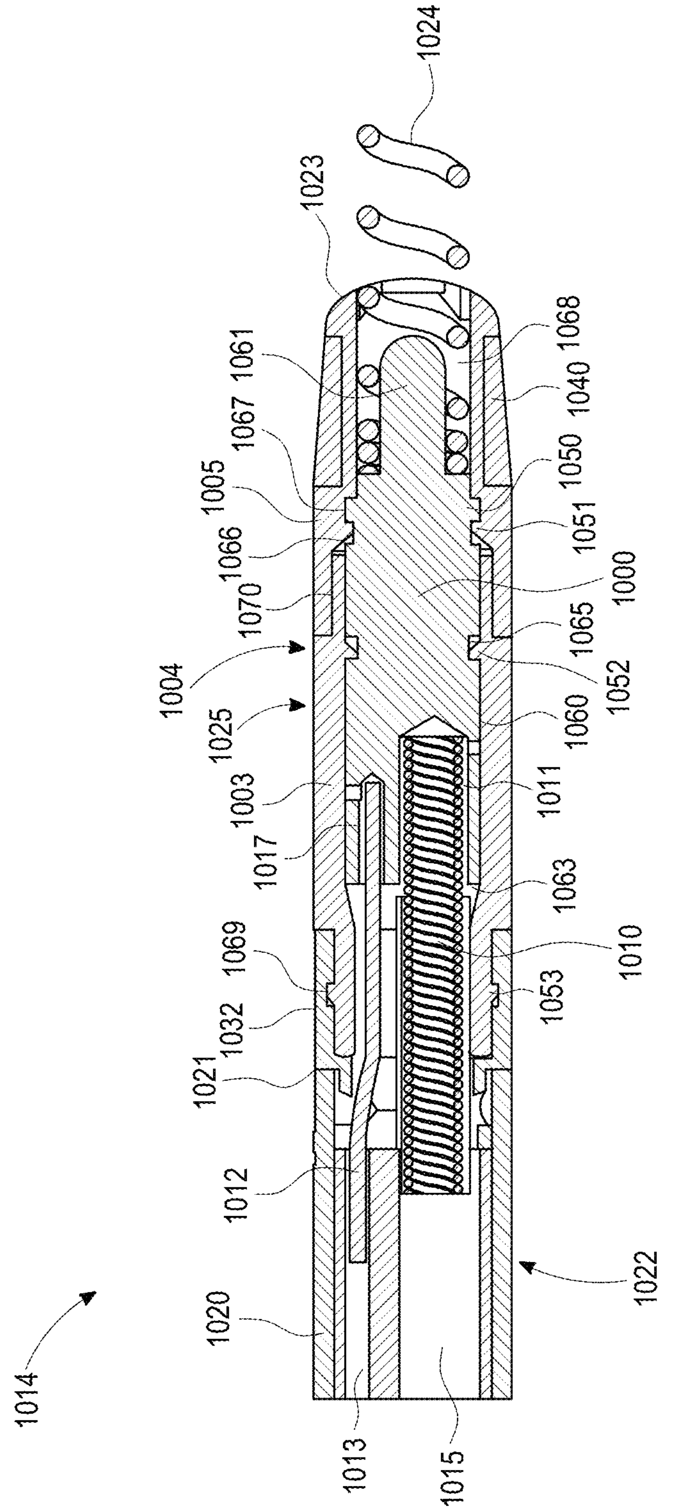
FIG. 11 is a partial cross-sectional view of a portion of an alternative lead, in accordance with an embodiment of the present disclosure.

FIG. 11 is a cross sectional view of another arrangement of a distal portion 1022 of lead 1014, in accordance with an embodiment of the present disclosure. In embodiments, the lead 1014 may be constructed in substantially the same manner as the leads 110, 514, 814 and 914 described above, except as described in connection with FIG. 10. In the illustrated embodiment, the lead 1014 includes a tubular lead body 1020 having proximal end (not shown) and a distal end 1021 opposite the proximal end. A distal assembly 1025 extends from the distal end 1021 of the lead body 1020. A first lead body lumen 1015 extends from the proximal end through the distal end 1021 of the lead body 1020, and a second lead body lumen 1013 extends from the proximal end through the distal end 1021 of the lead body. A first conductor 1010 is received within the first lead body lumen

1015, and a second conductor 1012 is received within the second lead body lumen 1013.

As shown, the distal assembly 1025 includes an outer shell 1004, a coupler 1000, a helical electrode 1024, and a ring electrode 1032. As further shown, the coupler 1000 is disposed and secured within the outer shell 1004, and the helical electrode 1024 has a portion disposed within the outer shell 1004 and extends distally from the outer shell 1004, as in other embodiments of the present disclosure. Additionally, in the illustrated embodiment, the outer shell 1004 includes a proximal shell component 1003 and a distal shell component 1005. The illustrated embodiment further includes a drug collar 1040 disposed over the distal shell component 1005. As shown, the drug collar 1040 decreases in diameter from proximal-to-distal, thus defining a tapered portion of the distal assembly 1025. In other embodiments, the outer shell 1004 is substantially isodiametric along substantially its entire length. As further shown, the distal tip 1023 is generally rounded or radiused to provide a relatively streamlined profile. When coupled with the tapered profile of the region just proximal to the distal tip 1023, the overall shape of the distal-most portion of the lead 1014 (other than the helical electrode 1024) takes on a bullet-shaped profile which can tend to provide better tissue-penetrating capabilities than a more blunt or flat-shaped distal tip.

The coupler 1000 is formed of an electrically conductive material and includes a proximal portion 1060 and a distal portion 1061. The proximal portion 1060 has an outer diameter that is larger than an outer diameter of the distal portion 1061. The coupler 1000 is disposed within the outer shell 1004. The coupler 1000 includes a proximal end 1063 and includes a first channel 1011 that extends distally from the proximal end 1063, forming a first blind hole. The first channel 1011 is configured to receive the first conductor 1010 and facilitate mechanically and electrically coupling the first conductor 1010 to the coupler 1000. A second channel 1017 extends distally within the proximal portion 1060 from the proximal end 1063, forming a second blind hole. As shown, the second channel 1017 is configured to receive the second conductor 1012 and to facilitate mechanically and electrically coupling the second conductor 1012 to the coupler 1000.

The proximal shell component 1003 is mechanically coupled to the proximal portion 1060 of the coupler 1000 by a first snap-fit connection. The first snap-fit connection is formed between a protrusion 1052 that extends from an inner surface of the proximal shell component 1003, and a mating recess 1065 on the outer surface of the coupler 1000. In some embodiments, as shown in FIG. 11, the protrusion 1052 may include a ramped or sloped distal surface to aid in the coupling process.

Additionally, the distal shell component 1005 defines a distal tip 1023 of the lead 1014 and is mechanically coupled to the proximal portion 1060 of the coupler by a second snap-fit connection. As shown, a protrusion 1051 extends radially inward from an inner surface of the distal shell component 1005 and mates with a corresponding recess 1066 on the outer surface of the coupler 1000. In some embodiments, as shown in FIG. 11, the protrusion 1051 may include a ramped or sloped proximal surface to aid in the coupling process. As further shown, the coupler 1000 also includes a circumferential flange 1050 that extends from the outer surface of the coupler 1000, and is received within a corresponding recess 1067 in the inner surface of the distal shell component 1005. Accordingly, the interaction of the protrusion 1051 with the recess 1066, and the circumferential flange 1050 with the recess 1067, form the second snap-fit connection.

As further shown, the arrangement of the distal outer shell component 1005, the distal portion 1061 of the coupler 1000, and the helical electrode 1024 defines a narrow cavity or space 1068 that can serve various functions, as will be explained in greater detail below.

As in the other various embodiments, the helical electrode 1024 includes a proximal portion that is disposed about the distal portion 1042 of the coupler 1000, and a distal portion that extends from the distal tip 1023 of the lead by a distance that can be selected to optimize the particular clinical needs for conduction system pacing, as described in connection with other embodiments. The helical electrode 1024 can receive or transfer electrical pulses to the IMD 12 (FIG. 1) via the coupler 1000 and the first conductor 1010 and/or the second conductor 1012.

The ring electrode 1032 is disposed partially over and mechanically coupled to the proximal shell component 1003 by a third snap-fit connection. The third snap-fit connection is formed by the interaction of a protrusion 1053 that extends from an outer surface of the proximal shell component 1003, and a corresponding recess 1069 on an inner surface of the ring electrode 1032. As shown, the proximal surface of the protrusion 1053 is ramped or sloped in a manner similar to the protrusion 1051 of the distal shell component 1005, which facilitates assembly of the ring electrode 1032 and the proximal shell component 1003.

As illustrated in FIG. 11, a portion 1070 of the distal shell component 1005 overlaps a portion of the proximal shell component 1003 when assembled. The overlap 1070 is positioned such that the first snap-fit connection is located proximal of the overlap 1070 and the second snap-fit connection is located distal of the overlap. During assembly of the distal assembly 1025, the proximal shell component 1003 may be advanced distally over the proximal portion 1060 of the coupler 1000 until the protrusion 1052 snaps into the corresponding recess on the coupler 100. The distal shell component 1005 may then be advanced proximally over the distal portion 1061 until the protrusion 1051 snaps into the corresponding recess on the coupler 100. Finally, the ring electrode 1032 may be advanced distally over the proximal shell component 1003 until the protrusion 1053 snaps into the corresponding recess on the ring electrode 1032.

The leads 814, 914, 1014 each have both a first electrical conductor and a second electrical conductor mechanically coupled to its respective coupler. In embodiments, the first conductors 810, 910, 1010 are coiled conductors that each define a coil conductor lumen sized to, among other things, receive a stylet or guidewire to facilitate accurate placement of the lead. In embodiments, the second conductors 812, 912, 1012 may comprise a solid or stranded-wire cable, which among other things, enhances the overall tensile strength of the respective lead, which can be advantageous if the lead must undergo tensile loading during extraction of the lead. In embodiments, both the coiled, first conductors and the second conductor in each lead may be electrically active, i.e., electrically coupled to circuitry within the pulse generator (FIG. 1) so as to provide a redundant electrical path between the pulse generator and the corresponding helical electrode. In alternative embodiments, only the coiled, first conductor in each lead is electrically active, and the second conductor is provided solely for structural purposes. Alternatively, in embodiments, the second conductor is electrically active, and the coiled conductor is present to provide the aforementioned coil conductor lumen for receiving a stylet or similar device to facilitate lead delivery and placement.

The various components of the leads of the present disclosure can be made from any known or later developed lead construction materials. For example, the lead body (e.g., the lead body 1020) can be made from any flexible, electrically insulative material suitable for human implantation. Exemplary materials for use as the body can include polyurethane, silicone rubber, and co-polymers of both, and can include surface or other treatments (e.g., plasma treatments, lubricious coatings, and the like) based on the functional requirements of the lead. The various conductors can also be made of any known or later developed lead conductor materials.

Similarly, the components of the distal assembly of the various leads described herein can be any known or later developed materials. In various embodiments, the outer shell materials can be selected from a range of non-electrically conductive material such as polyether sulfone (PES), polyurethane-based thermoplastics, ceramics, polypropylene and polyetheretherketone (sold under the brand name PEEK™). Additionally, the coupler (e.g., the coupler 1000) and the helical electrode (e.g., the helical electrode 1024) an be made of any known or later developed conductive material, typically a metal such as Elgiloy, MP35N, tungsten, tantalum, iridium, platinum, titanium, palladium, stainless steel as well as alloys of any of these materials. In various embodiments, helical electrode can include a surface treatment or coating, such as a coating of iridium oxide, to enhance the electrical performance of the helical electrode.

The implantable leads of the present disclosure are amenable to numerous design/feature variations tailored to enhance the performance, usability and deliverability of the respective leads. For efficiency, exemplary variations will be described with specific reference to the lead 1014 of FIG. 11, but the skilled artisan will readily recognize their applicability to other embodiments of the disclosure.

In embodiments, the design of the distal tip 1023 may be varied from that shown in FIG. 11 to provide capabilities uniquely adapted for conduction system pacing applications. For example, in embodiments, the inside surface of the distal tip 1023 may also be radiused (i.e., in addition to the outer surface).

In embodiments, the distal tip 1023 may be tapered more significantly than that shown in FIG. 11, effectively forming a relatively sharp point for enhancing tissue penetrating capability. Alternatively, the distal tip 1023 may be configured to have a relatively flat end (i.e., in a plane orthogonal to the longitudinal axis) to resist excessive tissue penetration. In such embodiments, the internal cavity 1068 embodiments, may be filled with a material to prevent tissue ingress. In one such embodiment, the filler material may be a drug-eluting material that can provide an alternative, or additional, drug eluting capabilities to the lead 1014. to provide a more blunt tip profile than that shown in FIG. 11.

In alternative embodiments, the distal tip 1023 may be formed of a soft material, or alternatively, may include a soft polymeric distal extension that is configured to fold or otherwise deform when the helical electrode is screwed into the target tissue, so as to resist excessive coring or tunneling into the target tissue.

In embodiments, the length of the distal shell component 1005 may be selected such that all or part of the distal portion 1061, as well as the portion of the helical electrode 1024 disposed thereabout, extends beyond the distal tip 1023, i.e., is exposed to and is capable of contacting tissue. In this way, the penetration depth of the active distal electrode component can be increased without increasing the length of the helical electrode 1024 itself. In still other embodiments, the distal shell component 1005 may be made from an electrically conductive material, and thus forms part of the distal electrode of the lead 1014.

In still further embodiments, other design variations of the distal shell component 1005 may be employed to affect tissue penetration during deployment of the helical electrode 1024. For example, in one embodiment, the distal tip 1023 may form a flange (not shown) that has an outer diameter greater than the outer diameter of the remainder of the distal shell component 1005. Optionally, this flange may be integrally formed with the distal shell component 1005, or alternatively, may be formed of a polymer material (which optionally may be configured to be drug-eluting) that is coupled to or formed on the distal shell component 1005. When present, this flange operates as a distal stop to delimit tissue penetration.

In embodiments, the lead body 1020 may have a larger diameter than the distal assembly 1025, with the transition therebetween forming a natural stop for delimiting penetration depth, e.g., by inhibiting migration of the distal assembly 1025 through the ventricular septum post-implantation. Additionally, or alternatively, tines or other passive fixation elements could be provided at lead body-to-distal assembly transition, e.g., at the distal end of the shocking coil (when present). In some embodiments, the entire distal shell component 1005 may be formed of a drug-eluting polymer material.

The design and functionality of the helical electrode of the various embodiments, e.g., the helical electrode 1024, can be selectively adapted for optimized conduction system pacing applications. In the various illustrated embodiments, the helical electrode 1024 has a generally uniform diameter along its length. In other embodiments, the helical electrode may vary in diameter along its length. In one embodiment, the outer diameter of the helical electrode 1024 increases in the proximal to distal direction. In such embodiments, the distal region of the helical electrode 2014 may effectively operate as a spring to resist excessive forward advancement into tissue. Alternatively, the outer diameter of the helical electrode 1024 may decrease in the proximal-to-distal direction to facilitate improved initial penetration of tissue during implantation. In still other embodiments, the diameter of the helical electrode may initially increase in the proximal-to-distal direction, then decrease toward the distal end of the helical electrode 1024. In any of the various embodiments, the distal portion of the helical electrode 1024 (i.e., the portion designed to penetrate the target tissue) may have a constant pitch, or a variable pitch, along its length.

In embodiments, the helical electrode 1024 may include a coating along a portion of its length. For example, in embodiments, the exposed portion of the helical electrode 1024 may be coated with a layer of polymer, e.g., parylene or comparable material to assist in tissue penetration. Alternatively, or additionally, a drug-eluting polymer coating may be applied over a portion of the helical electrode 1024.

In embodiments, a biodegradable covering, e.g., a mannitol cap, may be provided to encapsulate all or part of the distal portion of the helical electrode 1024 (i.e., the portion extending from the distal tip 1023) to further assist in the lead deployment (i.e., by minimizing the potential for the helical electrode to catch on tissue or delivery instruments, and to provide a protective cover to avoid damage to the helical electrode during advancement into the ventricle).

In embodiments, the outer surface of the coil conductor 1010 is encapsulated in an electrically insulative material, such as a polymeric sleeve or coating. In one embodiment, this outer sleeve or coating is made of a silicone material, although other materials may be utilized, e.g., ETFE, PTFE, polyurethane, and the like. When present, the outer sleeve or coating operates to mechanically support the coiled conductor 1010 in both axial tension (i.e., to inhibit the coiled conductor from stretching axially under tension) as well as under torsional loads (e.g., as when the lead 1014 is rotated to secure the helical electrical 1024 to tissue). In embodiments, the inner surface of the conductor 1010 is uncoated, which can be useful in the implantation procedure. For example, when a bare metallic stylet is inserted into the interior of the coiled conductor 1010, contact between the stylet and the inner surface of the conductor 1010 operates to provide electrical continuity between the stylet and the helical electrode 1024. As such, the stylet can be electrically connected to an ancillary device, such as a pacing system analyzer, and the helical electrode 1024 can then be used for mapping the target cardiac tissue.

In embodiments, the blind hole defined by the channel 1011 can also act as a stylet stop as well enable electrical coupling between a stylet and the helical electrode 1024, further enabling the stylet to be utilized for tissue mapping as described above. In embodiments, the coupler 1000 may include one or more features (e.g., a recess, slot, etc.) configured to receive and engage the end of the stylet within the channel 1011 to facilitate both delivery and extraction of the lead 1014. Exemplary such features are described in commonly-assigned U.S. Pat. No. 8,532,792, the entire contents of which are incorporated herein by reference.

In alternative embodiments, the distal assembly 1025 may be configured as an open-ended design, with a longitudinal lumen defined in part by the channel 1011 but extending through the distal portion 1061 of the coupler 1000. Such embodiments allow the lead 1014 to be delivered over a guidewire in a manner similar to conventional coronary venous leads.

In some embodiments, the conductor 1010 may include one or more radiopaque marker bands (not shown) selectively spaced along its length to provide allow the implanting clinician enhanced visualization of the distal portion 1022 during the implantation procedure. When present, the marker bands may be placed over the outer surface or the inner surface of the coiled conductor 1010. Additionally, or alternatively, radiopaque marker bands may be selectively disposed along an associated delivery stylet.

In various embodiments, the drug delivery mechanism may vary from the various drug collars described in the illustrated embodiments. For example, in embodiments, the drug collar (e.g., the drug collar 1040) may have radially-projecting ribs or rings on its outer surface to enhance tissue contact and fixation effectiveness. In embodiments, a drug delivery component may be disposed within the exposed distal portion of the helical electrode 1024, e.g., as a portion or extension of the distal portion 1061 of the coupler 1000. When present, this component may supplement or be provided in lieu of the drug collar 1040.

The particular embodiments illustrated herein and described above employ a single ring electrode (e.g., the ring electrode 1032), enabling bipolar pacing and sensing between the ring electrode and the helical electrode. The various embodiments are readily adaptable for other multipolar configurations. In embodiments, the various leads may be of quadripolar design, e.g., with three or more ring electrodes in addition to the helical electrode, which may be particularly advantageous for use in both right and left bundle branch pacing using a single lead.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable lead for use with an implantable medical device (IMD), the implantable lead comprising:
- a tubular lead body having proximal end, a distal end opposite the proximal end, a first lead body lumen extending from the proximal end through the distal end, and a second lead body lumen extending from the proximal end through the distal end;
- a proximal connector at the proximal end of the lead body configured for mechanically and electrically coupling the lead to the IMD;
- a distal assembly extending from the distal end of the lead body, the distal assembly comprising:
  - an outer shell having a proximal shell component and a distal shell component;
  - a coupler made of an electrically conductive material disposed within the outer shell and comprising a proximal portion having a proximal end and a first channel extending distally from the proximal end, and a distal portion opposite the proximal portion, wherein the proximal shell component is mechanically coupled to the proximal portion of the coupler by a first snap-fit connection, and the distal shell component is mechanically coupled to the proximal portion of the coupler by a second snap-fit connection; and
  - a helical electrode having a proximal portion disposed about the distal portion of the coupler, and a distal portion extending distally from the distal portion of the shell; and
- a first electrical conductor extending through the first lead body lumen and mechanically and electrically coupled to the coupler within the first channel.

2. The implantable lead of claim 1, wherein the coupler includes a second channel extending distally form the proximal end, and a third electrical conductor extends through the second lead body lumen and is mechanically and electrically coupled to the coupler in the second channel.

3. The implantable lead of claim 1, wherein the distal shell component overlaps the proximal shell component.

4. The implantable lead of claim 3, wherein the first snap-fit connection is located proximal of the overlap and the second snap-fit connection is located distal of the overlap.

5. The implantable lead of claim 1, wherein the distal shell component includes a collar impregnated with a drug or therapeutic.

6. The implantable lead of claim 1, wherein the coupler includes a first recess, a second recess, and a flange.

7. The implantable lead of claim 6, wherein the first snap-fit connection includes a proximal shell protrusion that mates with the first recess, the second snap-fit connection includes a distal shell protrusion that mates with the second recess.

8. The implantable lead of claim 6, wherein the distal shell includes a recess configured to receive the flange.

9. The implantable lead of claim 1, wherein the proximal portion of the coupler has a first diameter and the distal portion of the coupler has a second diameter.

10. The implantable lead of claim 9, wherein the first diameter is larger than the second diameter.

11. The implantable lead of claim 1, wherein the distal portion of the helical electrode extends from the distal portion of the shell a distance in the range of 0.5 mm to 2.5 mm.

12. The implantable lead of claim 1, wherein the distal shell component has an outer diameter that tapers from a proximal end to a distal end thereof.

13. The implantable lead of claim 1, further comprising a ring electrode and a third snap-fit connection, wherein the third snap-fit connection includes a proximal shell protrusion that mates with a recess on an interior of the ring electrode.

14. A distal assembly for a lead body, the distal assembly comprising:

an outer shell having a proximal shell component and a distal shell component;

a coupler made of an electrically conductive material disposed within the outer shell and comprising a proximal portion having a proximal end and a first channel extending distally from the proximal end and configured to receive a first electrical conductor, and a distal portion opposite the proximal portion, wherein the proximal shell component is mechanically coupled to the proximal portion of the coupler by a first snap-fit connection, and the distal shell component is mechanically coupled to the proximal portion of the coupler by a second snap-fit connection;

a helical electrode having a proximal portion disposed about the distal portion of the coupler, and a distal portion extending distally from the distal portion of the shell; and a ring electrode disposed partially over and mechanically coupled to the proximal shell component by a third snap-fit connection.

15. The distal assembly of claim 14, wherein the coupler includes a second channel extending distally from the proximal end and configured to receive a second conductor.

16. The distal assembly of claim 14, wherein the distal shell component overlaps the proximal shell component.

17. The distal assembly of claim 16, wherein the first snap-fit connection is located proximal of the overlap and the second snap-fit connection is located distal of the overlap.

18. The distal assembly of claim 14, wherein the distal shell component includes a collar impregnated with a drug or therapeutic.

19. An implantable lead for use with an implantable medical device (IMD), the implantable lead comprising:

a tubular lead body having proximal end, a distal end opposite the proximal end, a first lead body lumen extending from the proximal end through the distal end, and a second lead body lumen extending from the proximal end through the distal end;

a proximal connector at the proximal end of the lead body configured for mechanically and electrically coupling the lead to the IMD;

a distal assembly extending from the distal end of the lead body, the distal assembly comprising:

an outer shell having a proximal shell component and a distal shell component;

a coupler made of an electrically conductive material disposed within the outer shell and comprising a proximal portion and a distal portion opposite the proximal portion, the proximal portion having a proximal end, a first channel extending distally from the proximal end, and a second channel extending distally from the proximal end, wherein the proximal shell component is mechanically coupled to the proximal portion of the coupler by a first snap-fit connection, and the distal shell component is mechanically coupled to the proximal portion of the coupler by a second snap-fit connection; and a helical electrode having a proximal portion disposed about the distal portion of the coupler, and a distal portion extending distally from the distal portion of the shell;

a coiled first electrical conductor extending through the first lead body lumen and mechanically and electrically coupled to the coupler within the first channel; and a stranded cable second conductor extending through the second lead body lumen and mechanically and electrically coupled to the coupler within the second channel.

20. The implantable lead of claim 19, wherein the distal assembly further comprises a ring electrode disposed partially over and mechanically coupled to the proximal shell component by a third snap-fit connection.

* * * * *